(12) United States Patent
Millet

(10) Patent No.: US 7,951,103 B2
(45) Date of Patent: May 31, 2011

(54) ASSEMBLED ORTHOPEDIC RETRACTOR

(75) Inventor: Jean-Claude Millet, Etoile sur Rhône (FR)

(73) Assignee: Millet Innovation, Loriol sur Drome (FR)

(*) Notice: Subject to any disclaimer, the term of this patent is extended or adjusted under 35 U.S.C. 154(b) by 46 days.

(21) Appl. No.: 11/767,086

(22) Filed: Jun. 22, 2007

(65) Prior Publication Data

US 2007/0299382 A1 Dec. 27, 2007

Related U.S. Application Data

(63) Continuation of application No. PCT/FR2005/003187, filed on Dec. 20, 2005.

(30) Foreign Application Priority Data

Dec. 28, 2004 (FR) ..................... 04 13973

(51) Int. Cl.
*A61F 5/00* (2006.01)
*A61F 13/06* (2006.01)
*A43B 7/26* (2006.01)

(52) U.S. Cl. ............. 602/30; 602/5; 602/23; 36/94

(58) Field of Classification Search ............ 264/240, 264/225, 222, 219; 602/30, 13, 22, 23; 128/893, 128/892, 894, 889; 604/293; 132/73; 36/94
See application file for complete search history.

(56) References Cited

U.S. PATENT DOCUMENTS

| 2,503,656 | A | | 4/1950 | Cone | |
|---|---|---|---|---|---|
| 2,603,212 | A | | 7/1952 | Zeve | |
| 4,877,018 | A | * | 10/1989 | Ikebe et al. | 602/30 |
| 4,961,732 | A | * | 10/1990 | Stienstra | 604/293 |
| 5,340,352 | A | * | 8/1994 | Nakanishi et al. | 450/57 |
| 5,497,789 | A | * | 3/1996 | Zook | 128/893 |
| 6,183,452 | B1 | * | 2/2001 | Bodmer et al. | 604/308 |
| 2002/0095107 | A1 | * | 7/2002 | Martin | 602/61 |

FOREIGN PATENT DOCUMENTS

| FR | 2626170 A | * | 7/1989 |
|---|---|---|---|
| FR | 2626170 A1 | | 7/1989 |

* cited by examiner

*Primary Examiner* — Patricia M Bianco
*Assistant Examiner* — Ophelia Hawthorne
(74) *Attorney, Agent, or Firm* — Panitch Schwarze Belisario & Nadel LLP

(57) ABSTRACT

An orthopedic retractor is provided made of polymer gel shaped to be inserted into an interdigital space, having two complementary parts made of polymer gel, each part having a flat face shaped to be assembled to the flat face of the other part, such that together the two parts form the retractor, the flat faces once assembled forming a junction resistant to shearing forces while remaining separable from each other. Advantages: simplification of manufacturing and packaging methods.

11 Claims, 1 Drawing Sheet

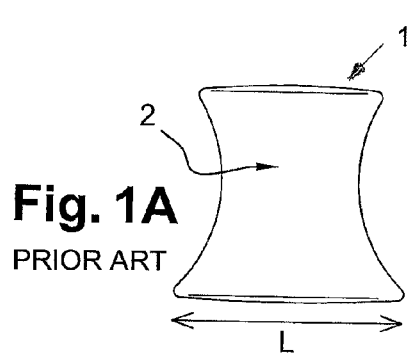
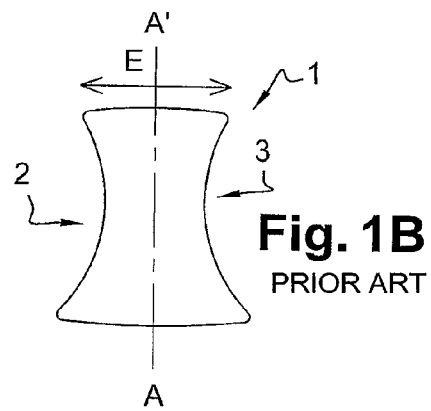
Fig. 1A PRIOR ART
Fig. 1B PRIOR ART
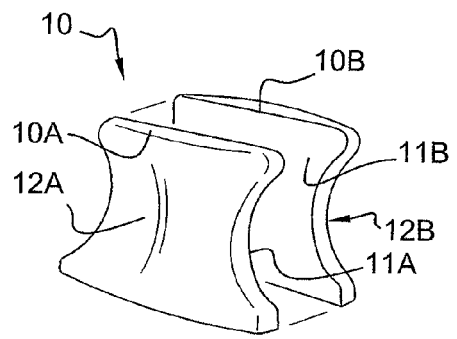
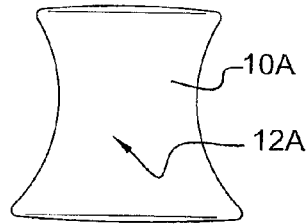
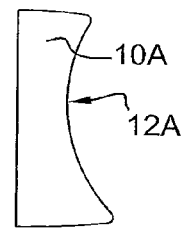
Fig. 2  Fig. 3  Fig. 4
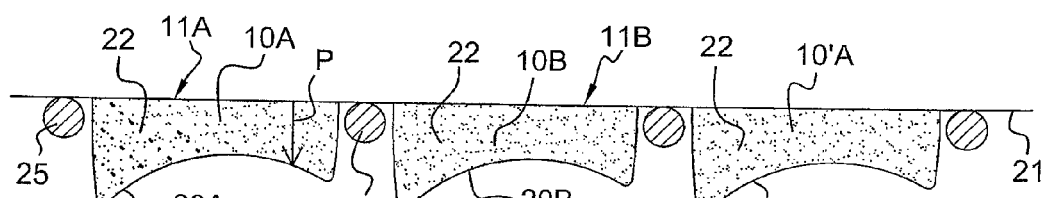
Fig. 5
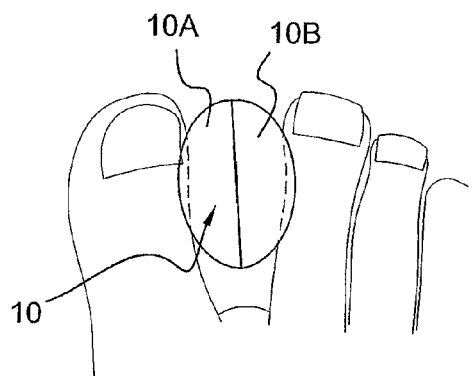
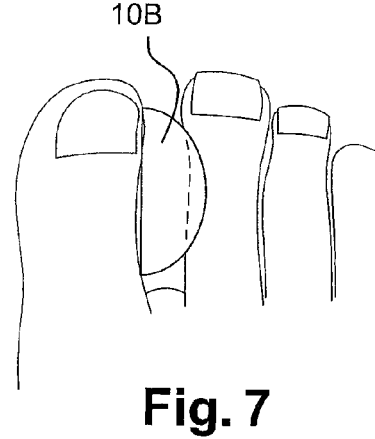
Fig. 6  Fig. 7

ASSEMBLED ORTHOPEDIC RETRACTOR

CROSS-REFERENCE TO RELATED APPLICATIONS

This application is a continuation of International Application No. PCT/FR2005/003187, filed Dec. 20, 2005, which was published in the English language on Jul. 6, 2006, under International Publication No. WO 2006/070098, the disclosure of which is incorporated herein by reference.

BACKGROUND OF THE INVENTION

The present invention relates to an orthopedic retractor.

Orthopedic retractors are commonly used to correct certain imbalances of the human foot, such as a Hallux Valgus (hyper-deviation of the big toe towards the outside) for example, or to prevent and relieve pain caused by a corn or a soft corn located at the bottom of the interdigital spaces. Thus, such retractors are inserted between the toes to be treated and enable the toes to be separated and spread open by a few millimeters.

Orthopedic retractors are generally made of silicone gel, for example a silicone gel marketed by Millet Innovation of Loriol Sur Drome, France, under the trademark Epithélium26®. They are very flexible, immediately comfortable and remain in place during the day, and they can be washed and reused.

The retractors generally have a shape which is imposed by the search for good morphological adaptation with the toes. Some have the shape of a marble, others have the shape of a tube, but the shape generally preferred is the shape referred to as "diabolo".

A classic retractor 1 of diabolo type is represented respectively by a side view and a profile view in FIGS. 1A and 1B. It can be seen that the diabolo shape is substantially different from the shape of the toy of the same name. It resembles that of a curved cylinder, having a smaller mid-height diameter (but non zero) than at its two ends, which has then been flattened by crushing to have a thickness E (profile view in FIG. 1B) corresponding to the distance that is wished to be imposed on the toes to be treated, and a length L (side view in FIG. 1A) shorter than the length of the toes.

The retractor 1 is thus intended to be arranged between two toes in the direction of its thickness E, and it has, in the direction of its length, two external lateral faces 2,3 that are substantially concave and which receive the edges of the toes.

Such a retractor is generally produced by means of a mold, into which the gel is introduced in liquid phase and then is cross linked (polymerized) before being removed from the mold. This manufacturing method is, however, expensive due to the cost of the mold, the steps of introducing the non-cross-linked gel into the mold and the steps of removing from the mold. In particular, the mold must have two parts which are joined in a sealed manner and which are then separated to extract the retractor from the mold.

Another disadvantage of such a retractor is that its thickness E is not necessarily suitable for all morphologies of feet and distances of toes to be treated, such that it must be made available in various models, which further increases its cost and price.

BRIEF SUMMARY OF THE INVENTION

Therefore, the present invention aims to provide a retractor which is simple to manufacture and with a reduced cost, as well as a method for manufacturing such a retractor.

The present invention is based on the observation that the gels used to produce retractors, and particularly silicone gels, although moderately adhesive on the skin, have the particular feature, when they are put in contact, of forming a junction that is highly resistant to shearing. Thus, if two flat surfaces made of cross-linked silicone gel are assembled against one another, the surfaces stick strongly in the presence of shearing forces (forces exerted in parallel to the two surfaces and which could make them slip in relation to one another) but stick only slightly when pulled apart perpendicular to their contact surfaces, such that they remain easy to remove.

The present invention is based on this property and provides for producing a retractor comprising two parts or "semi-retractors" each having a flat face intended to come into contact with the corresponding flat surface of the other part, and together forming the equivalent of a classic retractor. As the retractor is intended to be placed in an interdigital space, the two parts are further subjected to a force perpendicular to the contact faces, which increases the resistance of the assembly to shearing.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIGS. 1A and 1B are side and profile views of a classic retractor,

FIG. 2 is an exploded view of a retractor in two parts according to an embodiment of the present invention, FIG. 3 is a side view of one part of the retractor according to the embodiment of FIG. 2, FIG. 4 is a profile view of one part of the retractor according to the embodiment of FIG. 2, FIG. 5 is a cross-sectional view showing a method for manufacturing a retractor according to an embodiment of the present invention, FIG. 6 is a top view showing an example of use of a retractor according to an embodiment of the present invention, and FIG. 7 is a top view showing an example of isolated use of one part of a retractor according to an embodiment of the present invention.

DETAILED DESCRIPTION OF THE INVENTION

More particularly, the present invention provides an orthopedic retractor made of polymer gel intended to be inserted into an interdigital space, comprising two complementary parts made of polymer gel, each part comprising a flat face which is assembled or intended to be assembled to the flat face of the other part, so that together the two parts form the retractor, the flat faces once assembled forming a junction resistant to shearing forces while remaining removable.

According to one embodiment, the two parts are identical or symmetrical in shape and of the same thickness.

According to another embodiment, each part is made of silicone gel.

According to a further embodiment, the retractor comprises an active antibacterial or anti-inflammatory substance or a combination of the two active substances.

The present invention also relates to a method for manufacturing an orthopedic retractor comprising two parts made of polymer gel, each part comprising a flat face intended to be assembled to the flat face of the other part so that together the two parts form the retractor, the flat faces once assembled forming a junction resistant to shearing forces while remaining removable, the method comprising providing two open molds, a step of inserting the non-cross-linked polymer gel into each mold and a step of cross-linking the polymer gel in each mold, the molds being formed so that the open face of each mold corresponds to the flat face of each part.

According to one embodiment, the molds are formed by deformation of a plastic material.

According to another embodiment, the molds are formed by thermoforming of a plastic material.

According to a further embodiment, the method comprises a step of cutting the perimeters of each mold, so that each mold forms a package for each part of the retractor, and a step of packaging the parts in order to market them, by leaving them in their respective molds.

According to a still further embodiment, the method comprises a step of inserting an active antibacterial or anti-inflammatory substance, or a combination of the two active substances, into the non-cross-linked gel.

According to another embodiment, the molds are identical or symmetrical in shape.

The present invention also relates to an orthopedic object made of polymer gel intended to be inserted into an interdigital space to form a retractor or a separator, having a flat face intended to rest on a zone of the foot to be treated or to be protected and a concave face the function of which is to facilitate the holding of the object in the interdigital space.

According to one embodiment, the object is made of silicone gel.

According to another embodiment, the object comprises an active antibacterial or anti-inflammatory substance or a combination of the two active substances.

The present invention also relates to a method for manufacturing an orthopedic object made of polymer gel intended to be inserted into an interdigital space to form a retractor or a separator, the object having a flat face intended to rest on a zone of the foot to be treated or to be protected and a concave face the function of which is to facilitate the holding of the object in the interdigital space, the method comprising providing an open mold, a step of inserting the non-cross-linked polymer gel into the mold and a step of cross-linking the polymer gel in the mold, the mold being formed so that the open face of the mold corresponds to the flat face of the object.

According to one embodiment, the mold is formed by deformation of a plastic material.

According to another embodiment, the mold is formed by thermoforming of a plastic material.

According to a further embodiment, the method comprises a step of cutting the perimeters of the mold, so that the mold forms a package for the object, and a step of packaging the object in order to market it, by leaving it inside the mold.

According to a still further embodiment, the method comprises a step of inserting an active antibacterial or anti-inflammatory substance, or a combination of the two active substances, into the non-cross-linked gel.

It will be understood that the various embodiments described herein are not mutually exclusive, but one or more embodiments may be used together, where desired or appropriate.

A retractor 10 according to one embodiment of the present invention, as represented in FIG. 2, comprises two complementary parts 10A, 10B, each having a flat face 11A, 11B. Each part 10A, 10B is made of a polymer gel, preferably a silicone gel, such that the flat faces 11A, 11B stick to one another when they are assembled and form a polymer gel-to-polymer gel junction. As explained above, this adhesion, typical of the polymer gels, results in an excellent cohesion of the assembly in the presence of shearing forces tending to make the surfaces 11A, 11B slide in relation to another, while the surfaces 11A, 11B remain slightly adherent when pulled apart and can be separated after being put in contact. Now, the cohesion of the two parts in the presence of shearing forces is sufficient to meet the intended application since, when the retractor 10 is arranged in an interdigital space, the toes hold the two parts 10A, 10B between themselves and the parts essentially undergo only shearing forces.

The polymer or silicone gel is chosen so that its properties are on the order of those of the human tissues of the foot. The gel may be, for example, the abovementioned EPITHELIUM 26® or an equivalent material. In these conditions, the user no longer feels the presence of the retractor once the proprioceptive adaptation has occurred, i.e., after a few hours of use.

The shape represented in FIG. 2 is that of a diabolo retractor, which is the most commonly used, but the present invention can be applied to any shape of retractor. Thus, each part 10A, 10B has, opposite the flat faces 11A, 11B, substantially concave external faces 12A, 12B corresponding to the external faces 2, 3 of the classic retractor 1 represented in FIG. 1B and described above.

FIG. 3 represents the part 10A seen from the side of its external face 12A. Seen from this angle, the part cannot be distinguished from the classic retractor 1. On the other hand, in FIG. 4 which represents the profile view of the part 10A, it appears that the part 10A is the equivalent of one half of the classic retractor 1, which would have been obtained by cutting the retractor 1 along a longitudinal plane A-A' passing through the middle of the retractor 1.

However, and preferably, the parts 10A, 10B forming the retractor 10 are not obtained by cutting a classic retractor into two parts but by producing the two parts by means of two distinct molds, as it will now be described.

FIG. 5 shows a preferred embodiment of a method for manufacturing a retractor 10 according to the present invention. Open molds 20A, 20B are produced by printing hollow impressions in a fine sheet of plastic 21. These impressions correspond to the external shape of the parts 10A, 10B and particularly to the shape of the external faces 12A, 12B of the parts 10A, 10B. They are preferably produced by thermoforming (hot deformation) using an appropriate plastic, for example a polyethylene or PVC film.

The molds 20A, 20B can be of the same shape if the retractor 10 is symmetrical relative to a plane perpendicular to the faces 11A, 11B passing through the center of the retractor (which is the case in FIG. 2, the two molds here being identical). In the opposite case, if the retractor is only symmetrical relative to the faces 11A, 11B, they are of symmetrical and complementary shapes (each one forming the reflection of the other). Generally speaking, it is preferable for the parts 10A, 10B to be of the same thickness, such that the molds preferably have the same depth, i.e., a same depth P at similar points since the bottom of the molds is not flat due to the concave shape of the external faces 12A, 12B.

Once the molds 20A, 20B have been produced, the assembly is arranged on a support, for example a wired support comprising horizontal support bars 25 for supporting the plastic sheet 21, the bars 25 passing between the molds 20A, 20B. Such a method lends itself well to collective (mass) manufacturing of retractors according to the present invention, and various other molds 20'A (only one being represented) can be advantageously produced simultaneously on the plastic sheet 21.

A preparation of non-cross-linked liquid silicone gel 22 is then put into each of the molds, by filling the molds up to a determined level, to capacity in FIG. 5. This gel preparation advantageously comprises an active antibacterial or anti-inflammatory substance, so as to relieve pain caused by bone or articular imbalances by transdermal diffusion.

The liquid gel spreads out itself under the effect of gravity, such that the flat faces 11A 11B are obtained after cross-linking without the need to provide a step of cutting or reworking the parts produced.

In one advantageous embodiment of the method, the molds 20A, 20B are then cut without removing from the mold the parts 10A, 10B which are then packaged with their molds in transport packages, possibly after placing a thin protection sheet (not represented) on the open face of each mold. A larger protection sheet covering all the molds may also be welded or stuck onto the edges of the molds before the step of cutting and be cut with the molds to obtain a plurality of individual protective sheets.

FIG. 6 shows a use of the retractor 10 according to an embodiment of the present invention and represents the retractor 10 arranged between the big toe and the second toe. As indicated above, the compressive force exerted by the two toes holds the parts 10A, 10B in place and the shearing forces are cancelled out by the natural effect of adhesion between the two parts.

Advantageously, and as shown in FIG. 7, one of the two parts 10A or 10B can also be used alone as a toe separator (separation element without any spreading function) or as a retractor for small feet. Therefore, those skilled in the art will note that each part 10A or 10B according to the present invention-separator or retractor according to the size of the foot-forms in itself an object according to the present invention. Such an object differs from a separator or a classic retractor in that it comprises a flat face enabling the better distribution of load to be obtained on the zone of the foot to be protected or treated, and a concave face having a function of holding the object vertical.

Objects 10A, 10B according to the present invention, of different sizes and thicknesses, can also be combined to match various foot sizes, and/or to obtain spread values resulting from the combination of their dimensions by assembling for example objects 10A, 10B having different thicknesses.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An orthopedic retractor shaped to be inserted into an interdigital space of a foot, the retractor comprising two complementary parts made of a polymer gel, each part comprising a concave face adapted to cooperate with an edge of an adjacent toe of the foot, such that the retractor is self-maintained in the interdigital space without an additional securing means, and a polymer gel flat face which is assembled or to be assembled to the polymer gel flat face of the other part, such that together the two parts form the retractor, and such that the polymer gel flat faces once assembled form a polymer gel-to-polymer gel junction resistant to shearing forces while remaining separable from each other; wherein each part comprises the concave face both when the retractor is in a use position inserted into an interdigital space of a foot and when the retractor is in a non-use position not inserted into an interdigital space of a foot.

2. The retractor according to claim 1, wherein the two parts are identical or symmetrical in shape and have a same thickness.

3. The retractor according claim 1, wherein each part comprises silicone gel.

4. The retractor according to claim 1, further comprising an active antibacterial or anti-inflammatory substance or a combination of the two active substances.

5. The retractor according to claim 1, wherein each part comprises the concave face both when the retractor is in a use position inserted into an interdigital space of a foot and when the retractor is in a non-use position not inserted into an interdigital space of a foot.

6. A method for manufacturing an orthopedic retractor to be inserted into an interdigital space of a foot, the retractor comprising two parts made of polymer gel, each part comprising a concave face adapted to cooperate with an edge of an adjacent toe of the foot, such that the retractor is self-maintained in the interdigital space without an additional securing means, and a polymer gel flat face, the method comprising providing two open molds, inserting a non-cross-linked polymer gel into each mold, cross-linking the polymer gel in each mold, the molds being formed such that an open face of each mold corresponds to the flat face of each part, removing the parts from the molds and forming the retractor by assembling the parts by placing their respect polymer gel flat faces in contact with each other to form a polymer gel-to-polymer gel junction resistant to shearing forces while the parts remain separable from each other.

7. The method according to claim 6, wherein the molds are formed by deformation of a plastic material.

8. The method according to claim 6, wherein the molds are formed by thermoforming of a plastic material.

9. The method according to claim 6, further comprising cutting a perimeter of each mold such that each mold forms a package for one of the two parts of the retractor , and packaging the parts for marketing by leaving the parts in their respective molds.

10. The method according to claim 6, further comprising inserting an active antibacterial or anti-inflammatory substance, or a combination of the two active substances, into the non-cross-linked gel.

11. The method according to claim 6, wherein the molds are identical or symmetrical in shape.

\* \* \* \* \*